United States Patent [19]

Kleine-Homann

[11] Patent Number: 5,001,273

[45] Date of Patent: Mar. 19, 1991

[54] METHOD FOR PREPARING ASYMMETRIC ALIPHATIC KETONES

[75] Inventor: Walter Kleine-Homann, Duelmen, Fed. Rep. of Germany

[73] Assignee: Huls AG, Marl, Fed. Rep. of Germany

[21] Appl. No.: 319,875

[22] Filed: Mar. 1, 1989

Related U.S. Application Data

[63] Continuation-in-part of Ser. No. 165,800, Mar. 9, 1988, abandoned.

[30] Foreign Application Priority Data

Mar. 25, 1987 [DE] Fed. Rep. of Germany ....... 3709765

[51] Int. Cl.$^5$ .............................................. C07C 45/48
[52] U.S. Cl. .................................................. 568/397
[58] Field of Search ........................ 568/397, 354, 355

[56] References Cited

U.S. PATENT DOCUMENTS 3,468,956  9/1969  Mend ................................... 568/397
4,528,400  7/1985  Cryberg et al. ..................... 568/388

FOREIGN PATENT DOCUMENTS 0085996  8/1983  European Pat. Off. ............ 568/397
  55651  5/1967  Fed. Rep. of Germany ...... 568/397

OTHER PUBLICATIONS

Kirk–Othmer, "Encyclopedia of Chemical Technology" 2nd ed., vol. 12 (1967), p. 125.

*Primary Examiner*—James H. Reamer
*Attorney, Agent, or Firm*—Longacre & White

[57] ABSTRACT

A process for preparing asymmetric ketones by using a catalyst containing cerium oxide on an aluminum oxide support where the asymmetric ketones are prepared from carboxylic acid mixture at high conversions and good selectivity. The asymmetric ketones produced are for instance methyl-ethyl-ketone, ethyl-butyl-ketone, methyl-isopropyl-ketone or methyl-octyl-ketone.

14 Claims, No Drawings

METHOD FOR PREPARING ASYMMETRIC ALIPHATIC KETONES

This application is a continuation-in-part of application Ser. No. 07/165,800, filed 03/09/88, now abandoned.

CROSS REFERENCE TO A RELATED APPLICATION

Applicant claims priority under 35 USC 119 for application P 37 09 765.2 filed Mar. 25, 1987 in West Germany.

BACKGROUND OF THE INVENTION

The field of the invention is esters and processes of making same and the present invention is concerned with a method for preparing asymmetric aliphatic ketones. A mixture of two aliphatic carboxylic acids is reacted at higher temperatures in the presence of an oxidic metal catalyst to produce a ketone mixture in which the preparation of the desired asymmetric ketone is predominant as follows:

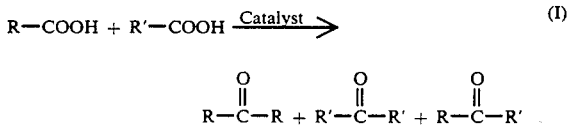

The state of the art of the synthesis given in equation (I) may be ascertained by reference to British Patent 1,194,057; French Patent 1,533,651; U.S. Pat. No. 3,468,956; TETRAHEDRAN LETT. 1972, pp. 257–260; and the Kirk-Othmer "Encyclopedia of Chemical Technology" 2nd Edition, Vol 12 (1967) p. 125.

As disclosed in British Patent 1,194,057, the initial input is an aldehyde in addition to the acid and the reaction takes place in the presence of water. Again in French Patent 1,533,651 costly aldehydes are used as initial inputs.

Another production method is described in TETRAHEDRAN LETT. 1972, pp 257–260. Therein suitable secondary alcohols are dehydrogenated into the corresponding ketones. The availability of the required secondary alcohol is problematical here.

Again, using a mixture of carboxylic acids to produce ketones has been described. U.S. Pat. No. 3,468,956 uses polyphosphoric acid in the temperature range between 100° and 300° C. as the catalyst. Many authors employ radioactive thorium oxide catalysts.

Kirk-Othmer i.b.i.d. discloses that unsymmetrical dialkyl ketones are prepared by passing vapors of two different fatty acids over an alkaline earth oxide at elevated temperatures. It is stated that the product necessarily contains the three possible ketones and in the example given a mixture of acetic acid and butyric acid are reacted in the vapor phase at 300° C. on a manganese dioxide catalyst to produce 16% methyl ethyl ketone, 24% propyl butyl ketone and 60% ethyl propyl ketone.

Accordingly the known methods require either initial substances which are costly at least in part, or catalytic systems which are commercially unsuitable.

SUMMARY OF THE INVENTION

Having in mind the limitations of the prior art it is an object of the present invention to produce asymmetric aliphatic ketones at satisfactory yields while using easily available initial materials and catalytic systems.

This object is achieved by reacting two aliphatic carboxylic acids at elevated temperatures in the vapor phase on an oxidic metal catalyst, wherein the reaction of the two aliphatic carboxylic acids is carried out at a molar ratio of 10 to 1:1 at temperatures between 320° and 550° C. on a catalyst containing cerium oxide and the crude product so obtained is fractionated.

A molar ratio of 4 to 2:1 is preferred where the ratio of the aliphatic carboxylic acid with the lower molecular weight predominates.

DESCRIPTION OF THE PREFERRED EMBODIMENTS

Surprisingly the preferred formation of asymmetric aliphatic ketones is made possible by the targeted use of two aliphatic carboxylic acids together with a catalyst containing cerium oxide, a reaction of 98 to 100% of the acid mixture being achieved The selectivity of formation of the asymmetric ketone, referred to the higher molecular carboxylic acid, as a rule is 40 to 60%. Following fractionation of the crude material, for instance in a multifil column, the asymmetric ketones are obtained with high purity, for instance a purity of 99.6%.

The catalyst is an aluminum oxide support charged with cerium oxide, preferably with about 5 to 25% and in particular 8 to 15% cerium oxide by weight. Whereas at lower cerium oxide concentrations and comparable reaction temperatures, a drop in reaction can be noticed, higher concentrations do not result in significant increases in activity. The reaction takes place at temperatures between about 320° and 550° C., preferably between 380° and 450° C. A noticeable loss in selectivity takes place at higher temperatures, whereas at lower ones, economic reaction no longer takes place.

Suitable input materials are alkyl carboxylic acids, both the straight chain type and the branched ones. Appropriately the acids used are mixed before metering. Obviously simultaneous but locally separate metered admixing of the particular pair of acids also is possible.

However, the desired quantitative proportions must be constantly monitored and assured because otherwise clear losses in yield will take place.

A molar ratio of the two acids of 10 to 1:1, preferably 4 to 2:1 was found practical, the acid with the lower molecular weight as a rule being predominant.

The asymmetric ketones so prepared are used as special solvents, scent components and scent pre-products.

The acid mixture starting materials are carboxylic acids with at least 2 hydrogen atoms at the alpha carbon atom which include acetic acid-propionic acid, propionic acid-valeric acid, and acetic acid-pelargonic acid and the products include methyl-ethyl-ketone, ethyl-butyl-ketone, and methyl-octyl-ketone.

EXAMPLES 200 ml of the contact catalyst are initially placed into a heatable quartz tube 0.5 m long and 26 mm in diameter. While nitrogen is being added, the filled amount is heated to the desired temperature (see Table). The temperature is measured by a resistance thermometer located in a centered quartz tube 6 mm in diameter, and can be axially displaced as desired. The prepared mixture of carboxylic acids then is heated by an evaporator with subsequent superheater to the desired temperature of reaction and is moved over the temperature controlled catalyst. The reactor discharge is condensed and analyzed by gas chromatography. As a rule the values are confirmed by fractionating the crude product in a 0.5 m multifil column. A conversion of the acid mixture of 98 to 100% is achieved by controlling the temperature of reaction.

| Example | Acid mixture | mixing proportion molar ratio | catalyst | temperature of reaction (°C.) | product | Selectivity* (%) | Purity (%) |
|---|---|---|---|---|---|---|---|
| 1 | acetic acid propionic acid | 1 1 | A | 450 | Methyl-ethyl-ketone | 42 | 99.0 |
| 2 | acetic acid propionic acid | 2 1 | A | 400 | Methyl-ethyl-ketone | 51 | 98.8 |
| 3 | acetic acid propionic acid | 4 1 | A | 420 | Methyl-ethyl-ketone | 48 | 99.2 |
| 4 | acetic acid propionic acid | 1 2 | A | 420 | Methyl-ethyl-ketone | 35 | 99.0 |
| 5 | propionic acid valeric acid | 2 1 | B | 430 | Ethyl-butyl-ketone | 36 | 98.5 |
| 6 | propionic acid valeric acid | 2 1 | C | 440 | Ethyl-butyl-ketone | 50 | 98.5 |
| 7 | propionic acid valeric acid | 2 1 | D | 420 | Ethyl-butyl-ketone | 46 | 98.8 |
| 8 Control | acetic acid isobutyric acid | 2 1 | A | 420 | Methyl-iso-propyl-ketone | 56 | 99.6 |
| 9 | acetic acid pelargonic acid | 3 1 | C | 420 | Methyl-octyl-ketone | 57 | 98.6 |

Catalyst
A 12% cerium oxide on aluminum oxide
B 1% cerium oxide on aluminum oxide
C 50 parts by weight catalyst
D + 50 parts by weight aluminum oxide
D 10% cerium oxide on aluminum oxide
*The selectivity of formation of the asymmetric ketone is referred to the higher molecular carboxylic acid

I claim:

1. In a process for preparing asymmetric ketones by reacting first and second aliphatic carboxylic acids at elevated temperatures on metal oxide catalyst, the improvement comprising:
said first and second carboxylic acids being selected from the group consisting of acetic acid, propionic acid, valeric acid and pelargonic acid and carrying out the reaction of said aliphatic carboxylic acids in the vapor phase at a molar ratio of said first acid to said second acid of 10 to 1:1 at temperatures between 320 and 550 degrees Celsius on a catalyst containing cerium oxide and fractionating the crude product obtained to separate said asymmetric ketone.

2. The process of claim 1, wherein said cerium oxide catalyst is 5 to 25% by weight cerium oxide on an aluminum oxide support.

3. The process of claim 1, wherein said cerium oxide catalyst is 8 to 15 % by weight cerium oxide on an aluminum oxide support.

4. The process of claim 1, wherein said reaction is carried out at a molar ratio of said carboxylic acids of 4 to 2:1.

5. The process of claim 2, wherein said reaction is carried out at a molar ratio of said carboxylic acids of 4 to 2:1.

6. The process of claim 3, wherein said reaction is carried out at a molar ratio of said carboxylic acids of 4 to 2:1.

7. The process of claim 1, wherein said reaction is carried out at temperatures between 380° and 450° C.

8. The process of claim 4, wherein said reaction is carried out at temperatures between 380° and 450° C.

9. The process of claim 1, wherein said aliphatic carboxylic acids are mixed before the reaction.

10. The process of claim 1, wherein said second aliphatic carboxylic acid has a higher molecular weight than said first aliphatic carboxylic acid.

11. The process of claim 9, wherein 98 to 100% of said mixture is reacted.

12. The process of claim 1, wherein said first carboxylic acid is acetic acid and said second carboxylic acid is propionic acid.

13. The process of claim 1, wherein said first carboxylic acid is propionic acid and said second carboxylic acid is valeric acid.

14. The process of claim 1, wherein said first carboxylic acid is acetic acid and said second carboxylic acid is pelargonic acid.

* * * * *